United States Patent [19]

Mathews

[11] Patent Number: 5,496,322

[45] Date of Patent: *Mar. 5, 1996

[54] METHOD FOR SUBCUTANEOUS SUPRAFASCIAL PEDICULAR INTERNAL FIXATION

[75] Inventor: Hallett H. Mathews, Richmond, Va.

[73] Assignee: Danek Medical Inc., Memphis, Tenn.

[ * ] Notice: The term of this patent shall not extend beyond the expiration date of Pat. No. 5,171,279.

[21] Appl. No.: 279,222

[22] Filed: Jul. 22, 1994

Related U.S. Application Data

[60] Continuation of Ser. No. 267, Jan. 1, 1993, abandoned, which is a division of Ser. No. 938,308, Sep. 1, 1992, abandoned, which is a division of Ser. No. 852,577, Mar. 17, 1992, Pat. No. 5,171,279.

[51] Int. Cl.$^6$ .................. A61H 7/00; A61F 2/44
[52] U.S. Cl. .................. 606/61; 623/17
[58] Field of Search .................. 623/66, 17, 16, 623/18; 606/61; 128/898

[56] References Cited

U.S. PATENT DOCUMENTS

| | | |
|---|---|---|
| 3,892,232 | 7/1975 | Neufeld . |
| 3,964,480 | 6/1976 | Froning . |
| 4,545,374 | 10/1985 | Jacobson . |
| 4,573,448 | 3/1986 | Kambin . |
| 4,616,638 | 10/1986 | Griggs . |
| 5,062,845 | 11/1991 | Kuslich et al. . |
| 5,158,543 | 10/1992 | Lazarus .................. 606/191 |
| 5,171,279 | 12/1992 | Mathews .................. 606/61 |
| 5,357,983 | 10/1994 | Mathews .................. 606/61 |

OTHER PUBLICATIONS

Spine Instrumentation—Harrington; by Paul R. Harrington, MD. (all).
ISOLA Spinal Implant System—Principles and Practice; Marc A. Asher, MD. Walter E. Strippgen, Charles F. Heinig, MD., William L. Carson PhD (brochure–all).

*Primary Examiner*—David Isabella
*Attorney, Agent, or Firm*—Woodard, Emhardt, Naughton, Moriarty & McNett

[57] ABSTRACT

A method for internal fixation of vertebra of the spine to facilitate graft fusion includes steps for excising the nucleus of an affected disc, preparing a bone graft, instrumenting the vertebrae for fixation, and introducing the bone graft into the resected nuclear space. Disc resection is conducted through two portals through the annulus, with one portal supporting resection instruments and the other supporting a viewing device. The fixation hardware is inserted through small incisions aligned with each pedicle to be instrumented. The hardware includes bone screws, fixation plates, engagement nuts, and linking members. In an important aspect of the method, the fixation plates, engagement nuts and linking members are supported suprafascially but subcutaneously so that the fascia and muscle tissue are not damaged. The bone screw is configured to support the fixation hardware above the fascia. In a further aspect of the invention, a three component dilator system is provided for use during the bone screw implantation steps of the method.

4 Claims, 2 Drawing Sheets

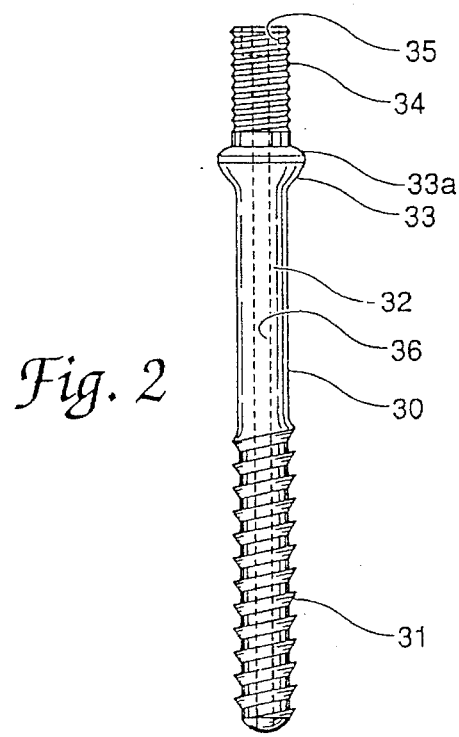
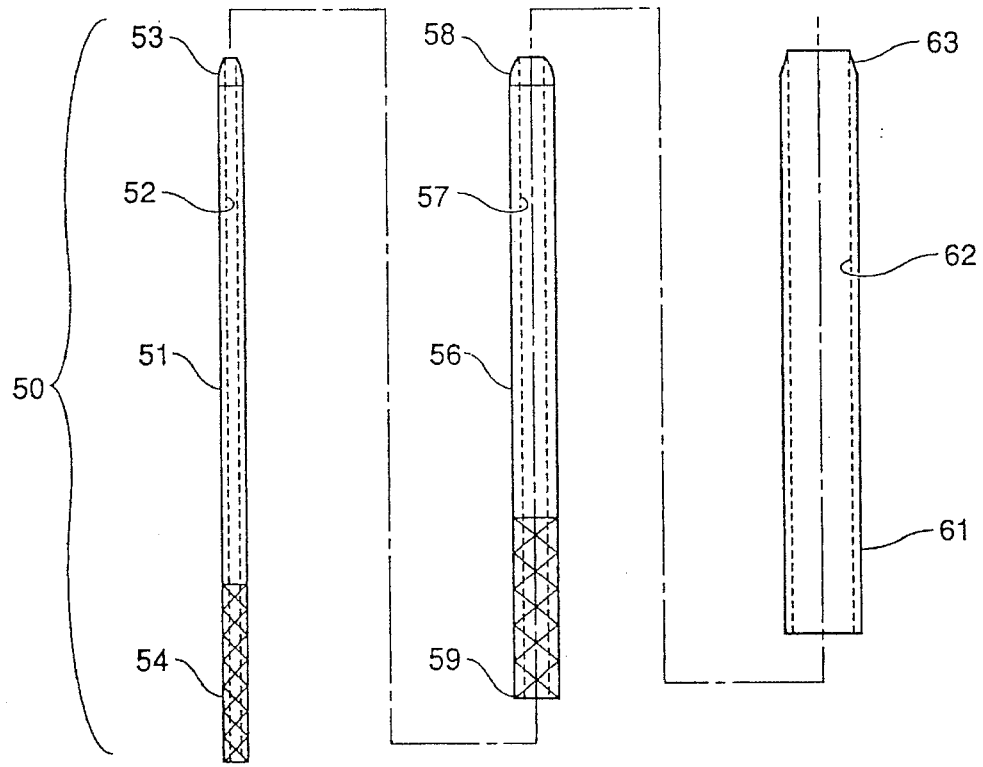

METHOD FOR SUBCUTANEOUS SUPRAFASCIAL PEDICULAR INTERNAL FIXATION

This application is a continuation of application Ser. No. 08/000267, filed Jan. 1, 1993, now abandoned, which is a divisional of application Ser. No. 07/938,308, filed Sep. 1, 1992, now abandoned, which is a divisional of application Ser. No. 07/852,577 filed Mar. 17, 1992 which issued as U.S. Pat. No. 5,171,279.

BACKGROUND OF THE INVENTION

The present invention concerns a method for internal fixation of vertebra of the spine.

It has long been known that internal fixation is an adjunct to fusion, such as a transverse process fusion. In early prior art techniques, a surgeon made an incision in the patient's back and separated tissue and muscle in order to expose a wide area of the spine in which the procedure was to take place. The fusion and fixation in one prior art process is by grafting bone segments between opposing transverse processes of adjacent vertebrae. However, this technique resulted in gross destruction of normal anatomy as well as high blood loss. Moreover, this surgical technique did not completely stabilize the vertebra since there was no direct connection between the vertebral bodies.

In more recent times, a surgical technique known as dowel interbody fusion has been developed. In this technique, bores are formed in disc tissue through either open surgery or percutaneous surgery. A dowel is made to fit into the bores formed in the disc tissue. In still a further technique, all disc tissue is removed between adjacent vertebrae, as well as the disc plates. Large surface area bone grafts are then placed within the clean space to form a graft between the opposing vertebral bodies. In each of these latter two prior art processes it still remains necessary to provide some means for fixation to facilitate fusion of the large area bone graft or the dowel to the vertebrae.

Many types of instrumentation for performing spinal fixation are known in the art. For instance, spine instrumentation developed by Harrington incorporates a hook and rod configuration. Implantation of tile Harrington spinal instrumentation requires subperiosteal stripping of the spine to avoid injury to the muscular nerves and vessels. Dissection of the muscle tissue is also required in some aspects of the early Harrington techniques, the spine was stripped clean of the supraspinous and intraspinous ligaments.

Later developed techniques involve hardware which is placed through the skin and through the muscle into the bone. Some of the fixation hardware remains outside the body, but is removed after tile fusion has been completed. Techniques of this sort are characterized by high risk of pin tract infection and incisional morbidity.

Thus far, each of the prior art spinal fixation and/or fusion techniques have been characterized by excessive invasion into the patients spine and back region. What is needed is a technique which allows for adequate stabilization of the spine, yet decreases the chance of infection as well as patient morbidity. There is further a need for such a method which permits percutaneous removal of the fixation hardware as an outpatient procedure after fusion has been completed.

SUMMARY OF THE INVENTION

The present invention contemplates a percutaneous fusion technique using subcutaneous suprafascial internal fixation. More particularly, the minimally invasive technique of the present invention permits anterior fusion of the disc space of the lumbar spine following appropriate disc resection and bone grafting. The fixation process is suprafascial, that is above the muscle fascia, but subcutaneous, that is beneath the surface of the skin. Thus, none of the muscle tissue is destroyed and the subcutaneous nature of the procedure greatly decreases the risk of pin tract secretions or infections, or the potential of osteomyelitis.

In more specific aspects of the invention, the technique contemplates first resecting the intranuclear cavity of a damaged disc, including ablation of the superior and inferior end plates. Bone graft material is prepared for introduction into the vacated disc space. Prior to introduction of the bone graft into the empty disc nuclear space, fixation instrumentation is implanted. In general, this fixation hardware can include self-tapping cannulated bone screws, fixation plates and linking members for laterally fixing plates on opposite sides of the spinous process.

In the preferred method, guide wires are inserted bilaterally in line with and into the pedicle. Pedicle screws are advanced over the guide wire and engaged into a predrilled bore in the pedicle. After the guide wire is removed, the skin is elevated and tissue in the suprafascial subcutaneous space is dissected to permit insertion of the fixation plates. The appropriate plates are first engaged over the ipsilateral screws and then the procedure is repeated for the contralateral bone screws at each level of hardware, that is at each vertebra to be stabilized. The bilateral fixation plates can be laterally connected by dissecting across the midline between corresponding screws and then positioning a linking member between the screws using a top-loading insertion mechanism. A nut is also top-loaded on to each successive screw to secure the linking members to the plate and to secure the plate to the pedicle screws.

In the inventive method, the nuts engaging the pedicle screws are initially loosely threaded onto the screws. The bone screws are then advanced into the vertebral body until the hardware resides below the level of the skin, but suprafascially in the subcutaneous space at each level of the instrumentation. The nuts are then tightened when they fixation hardware is in its final resting spot. Once the fixation instrumentation is in position, the bone graft material is introduced through a cannula to the disc space and moved into position by an obturator. With the bone graft in place and the spinal fixation hardware engaged to the appropriate vertebrae, the subcutaneous tissue is then irrigated and closed.

In another aspect of the invention, a cannulated fixation or bone screw is provided which is well suited for use with the inventive method. More specifically, the screw includes a distal threaded shank and a proximal nut threaded stem which terminates in a driving hub. The distal threaded shank includes self-tapping bone engaging threads. Intermediate the threaded shank and the stem is a smooth shank of sufficient length so that only the smooth shank contacts muscle tissue when the fixation instrumentation is in place. Near the stem end of the smooth shank is a mounting hub which supports the fixation plate before the nut is engaged on the threaded stem. The smooth shank preferably accounts for about one-half of the length of the screw as measured from the tip of the bone engaging threaded shank to the underside of the mounting hub.

In a further aspect of the invention, a three component dilator system is provided to facilitate instrumentation of the vertebrae. In particular, the dilator system includes three concentrically disposed hollow dilator tubes, each tapered at its respective end for atraumatic introduction into the patient. Each of the three dilators is successively smaller in diameter but larger in length. The intermediate and smallest dilator tubes have hurled ends to grasp for removal during steps of the method.

It is one object of the present invention to provide a method for internal fixation of the spinal column which is minimally invasive and which poses a minimal health risk to the patient. Another object is to provide such a technique which further permits subcutaneous removal of the temporarily implanted hardware in an out-patient procedure.

A further object of the invention is realized by the present technique which contemplates subcutaneous but suprafascial fixation to avoid damage to the spinal musculature and ligaments. Further objects and certain advantages of the present invention will become apparent from the following description of the invention.

DESCRIPTION OF THE DRAWINGS

FIG. 2 is a side view of a bone screw adapted for use in the method of the present invention.

FIGS. 4A–C are side views of the components of a three component dilator system for use with the method of the present invention during steps for implanting the bone screw into a vertebra.

DESCRIPTION OF THE PREFERRED EMBODIMENT

Figure 1:
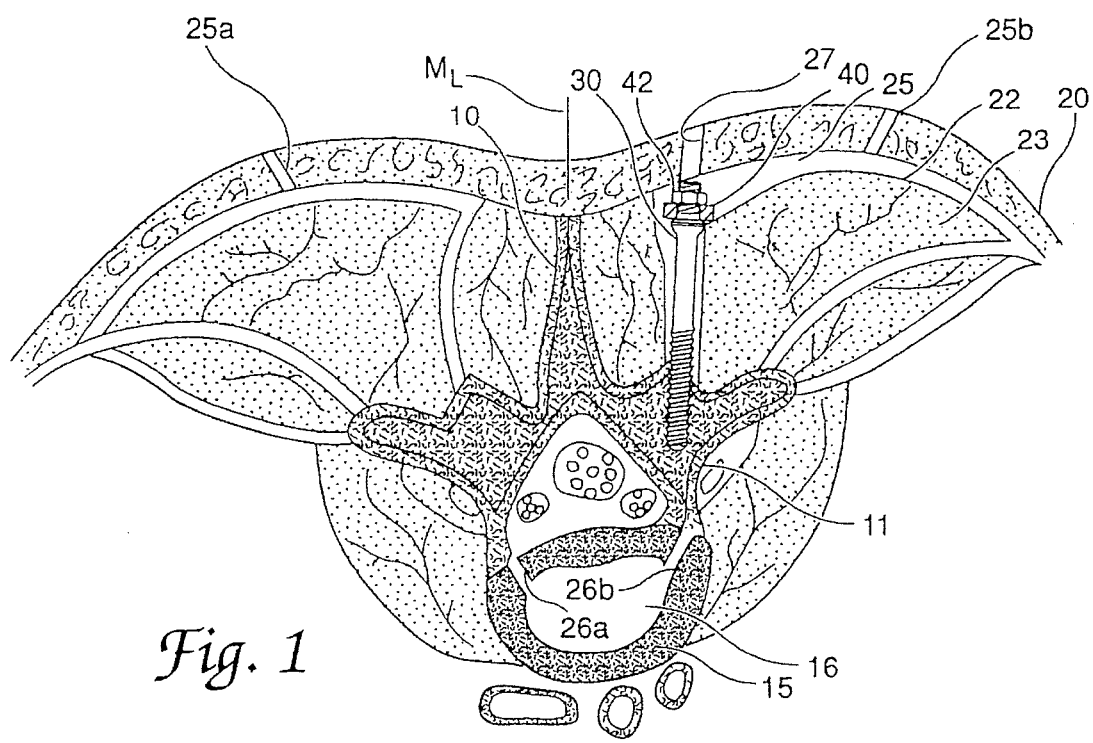
FIG. 1 is a section view through the spinal column of a patient shown after implantation of fixation instrumentation using the method of the present invention.

For the purposes of promoting an understanding of the principles of the invention, reference will now be made to the embodiment illustrated in the drawings and specific language will be used to describe the same. It will nevertheless be traderstood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention first contemplates steps for a percutaneous fusion technique, such as may be used to fuse adjacent vertebrae after disc tissue has been removed. According to the preferred embodiment of the invention, the method is conducted on lumbar vertebrae, although it is believed to be adaptable to other portions of the spine. The patient, after appropriate preparation, is positioned prone on a radiolucent padded frame which allows for both AP (anterior/posterior) and lateral fluoroscopic visualization during the entire procedure. An initial AP fluoroscopic view is taken with an external guide pin placed parallel to the plane of the end-plates of the affected disc to assure the proper orientation of the procedure relative to the disc space. A guideline is drawn on the AP radiograph along the guidepin image to demarcate the plane of entry.

In the preferred embodiment of the fusion technique of the present method, a bi-portal approach is utilized to clean out the disc nuclear space. Entry points for local anesthesia are located bilaterally from the midline, nominally about ten centimeters bilaterally from the radiograph guideline (varying between 8 centimeters for a smaller patient to 12 centimeters for a larger patient).

After the fascia and intrafascia musculature are appropriately anesthetized, discography is performed using a two-needle technique bilaterally. Pursuant to the preferred method, the initial needle entry point to the disc annulus is located on the mid-pedicle line on the AP radiograph, which is defined by the line created by the midportion of the pedicle above and below the disc space being instrumented. Both needles are advanced into the posterior central portion of the nucleus and triangulation is begun. The discography is performed to confirm the nature of the disc disease and the contained verses the uncontained condition of the involved disc structure. (An uncontained disc is a disc which has ruptured through the posterior longitudinal ligament and/or annulus, which therefore allows a free flow of dye from the intranuclear space into the epidural space.)

The procedure of the preferred method continues with the introduction of cannulae into the disc space. The hubs of the discogram needles can be removed and then serve as guide wires for the cannulae. Dilating probes are place over the guide wires bilaterally into the annulus of the disc. Sheaths are placed over the probes over which progressively larger cannulae can then be advanced to dilate the annulus to an appropriate diameter for intradiscal work. Again, this prior procedure is performed bilaterally at the two entry points described above, and is repeated for each affected disc.

In one aspect of the method, a visualization scope is place through each cannula to verify the annulus and to confirm the anatomy under the cannula. If no nerve tissue is observed and the annular tissue is present, a trephine is introduced after the visualization scope has been removed. The annulus is perforated and successively sized trephines are used to open an annular hole of adequate dimension for the purpose of disc removal and extra-discal visualization.

Once the trephine operation is complete at each bilateral entry point, two portals are provided. Disc resection can be conducted through one portal while a verifying scope can be placed at the other portal. Triangulation of the disc material through one portal is considered achieved when direct visualization of the disc resecting instrument occurs through the viewing portal. The intranuclear cavity of the affected disc is completely resected and the superior and inferior end-plates are ablated using cutting and sucking instruments or through the use of laser-assisted probes. The instruments may be removed from each portal and transposed for complete resection of the disc nucleus. Rapid disc removal instruments for the nucleus and rapid burring devices for the end-plates can be used to resect the tissues in preparation for fusion. The instruments may also be used to resect the posterior ligamentus structures and the interannular ring to create an adequate cavity for introduction of the bone graft. Acceptable devices include burrs, laser, curettes and gauges for the ablation of the end-plate tissues to the state of bleeding bone. Both rigid and flexible scopes can be used for the verification of the complete resection of the intranuclear cavity. Once the disc material has been completely cleared out of the cavity and the end-plates completely ablated, and obturator is placed in each cannula to prevent contamination during this succeeding portions of the procedure.

At this point of the preferred technique of the present invention, bone graft harvesting is undertaken. The bone graft harvesting can be accomplished according to any known techniques suitable for this purpose. In one specific embodiment of the inventive method, after appropriate anesthesia and analgesia, a small incision is made over either posterior superior iliac crest to expose the outer crest for bone harvesting. The bone is procured from the corticocancellous table and prepared for the grafting process. The bone graft is fashioned to be accommodated within the inner diameter of the largest outer cannula employed during the disc resection described above. The bone may be mixed with other components, including osteoinductive proteins or morphogenic materials. The bone harvest cite is then irrigated, dried and closed over a small drain.

The next step of the inventive process, the instrumentation step, occurs under direct fluoroscopy. Under AP fluoroscopic view, a guide wire (preferably a 0.062 guide wire is introduced with the sharp end of the guide wire being inserted into the skin at a position slightly offset from the area to be cannulated. In one specific embodiment, the guide wire is introduced one centimeter lateral to the area to be cannulated. The position of the guide pin is verified by fluoroscopy angled to 15 degrees in line with the pedicle. The guide pin is used to palpate the cortex over the pedicle and is then secured by tapping with a mallet to prevent movement of the pin until further advancement is desired. After the guide pin has been locked into the cortex, tissue dilators are applied to protect the surrounding muscle tissue. The guide pin is then advanced, under lateral fluoroscopic view, into the pedicle and within the vertebral body. The position of the pin is confirmed using both AP and fluoroscopy views. This procedure is repeated for each pedicle o the vertebra. Thus, for each vertebra to be instrumented, a pair of guide pins are positioned at about a 15° angle from the midline and along each pedicle of the vertebra.

After the guide pin insertion process is complete, an incision is made at the guide pin insertion site, which, in one specific embodiment, is about 2.0 cm. in length. Then, using pick-ups and Metzenbaum scissors, subcutaneous tissue is dissected suprafascially. Metzenbaum scissors are also used to dissect the suprafascial subcutaneous tissues from the ipsilateral pin across the midline to the contralateral guide pin. Dissection of this tissue provides space for connection of pedicle screws in subsequent steps of the method.

In the next step of the inventive method, a three component tissue dilator system is used to dilate the tissue at each guide pin to accept first a cannulated drill bit and then a larger diameter cannulated self-tapping bone screw. The dilator system comprises three tapered tubes of increasing diameter and decreasing length. The tubes are introduced successively from smallest diameter to largest diameter to provide adequate access through the tissue for later steps of the method. After the three component tissue dilator system has been inserted, the smallest of the internal dilators is removed allowing for insertion of the drill bit along the guide pin. The bit is used to drill into the initial one-third of the pedicle. The bit is removed and the intermediate tissue dilator is then removed, leaving the largest dilator still in place. The self-tapping bone screw is inserted through the largest dilator over the guide wire until it is advanced to at least 50% depth of the pedicle. After the position of the bone screw has been confirmed by lateral fluoroscopy, the guide wire is removed and the screw advanced until the proximal tip of the screw is at the level of the skin incision. This procedure is repeated for each pedicle in each successive vertebra until all the bone screws are in place for the final internal fixation instrumentation.

In one specific embodiment, the cannulated drill bit has an outer diameter of 4.5 mm, while the cannulated bone screw can have a diameter between 5.5–8.5 mm. Thus, in this specific embodiment, the intermediate dilator of the three component dilator system has an internal diameter of at least 4.5 mm, and preferably 5.2 mm to receive the drill bit therethrough. Likewise, the largest dilator has an internal diameter at least larger than the bone screw, and preferably 9.6 mm to accommodate a range of bone screw diameters.

Pick-ups are again used to elevate the skin and Metzenbaum scissors are used to dissect any remaining subcutaneous suprafascial tissue as required to accommodate insertion of an elongated fixation plate. An appropriately sized fixation plate is inserted using forceps through the 2.0 cm. incisions. It is understood that the fixation plates are sized to fit over bone screws engaged in the pedicles of adjacent vertebrae to provide adequate fixation at each side of the spinous process. The fixation plates for the ipsilateral screws are first inserted by forceps and then the procedure is repeated for the contralateral side at each vertebral level requiring instrumentation. In addition, linking members are inserted through the incision at the ipsilateral guide pin and passed across the midline in the subcutaneous space to engage the ipsi- and contra- lateral bone screws to accomplish trans-lateral linkage. The linking member can be of the type sold by Danek Medical, Inc., assignee of the present invention, as its CROSSLINK™ product. Once each of the fixation plates and linking members have been engaged over the appropriate bone screws, a nut is applied in a top-loaded fashion to loosely secure the hardware together.

After each nut is initially threaded onto its corresponding screw, the bone screws are advanced as necessary so that all of the fixation hardware lies subcutaneously, but suprafascially, at each level of the instrumentation. Once each of the bone screws has reached its final resting place within the vertebra, and once all the instrumentation, including the fixation plates and linking members, is within the appropriate suprafascial subcutaneous space, the nuts are tightened, while the bone screws are held, at each successive level, thus creating a firm interlock between all of the components of the fixation system. AP and lateral fluoroscopic views can document the final position of the hardware to the satisfaction of the operating surgeon.

Once the fixation instrumentation has been inserted, each bone screw insertion cite is thoroughly irrigated as well as the subcutaneous space which has accepted the fixation components. The incisions are dried and hemostasis verified followed by closure of the incision with subcutaneous absorbable sutures.

With the fixation hardware in place, attention is returned to the prior portals through which the disc resection was conducted. In this step of the method of the present invention, the obturators are removed from the portals and the previously harvested bone graft material is introduced through one cannula into the disc space. A visualizing scope is extended through the cannula in the other portal for confirmation of entry of the bone graft into the disc space. A smooth obturator is inserted into the cannula to facilitate advancement of the bone graft material through the cannula into the empty disc nuclear space. After the ipsilateral portal has been completely filled with bone graft material, the same procedure is performed at the contralateral portal. Visual verification of the grafting procedure in the contralateral portal is not possible because the first portal has been filled by graft material. However, fluoroscopy can be used to identify the introduction of the obturator into the disc nuclear cavity, thereby confirming the location of the bone graft material. Upon completion of the grafting process, the cannulae are removed, the subcutaneous tissue irrigated and the discography entry points are closed with absorbable sutures.

Figure 3:
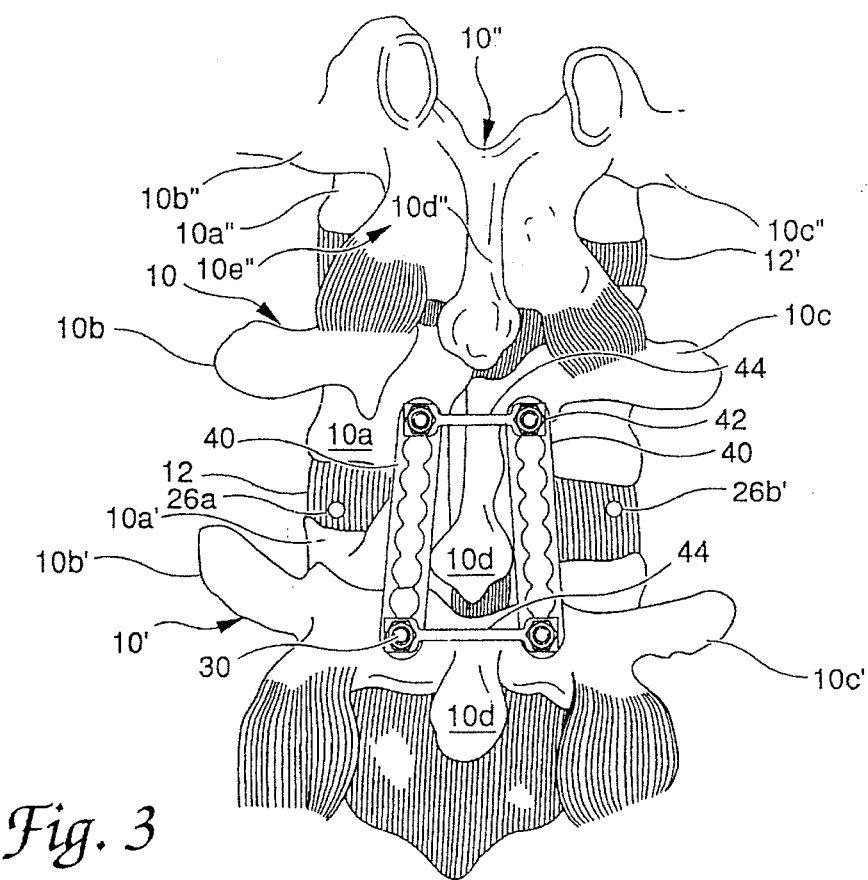
FIG. 3 is a posterior view of the spinal column of the patient after implantation of fixation instrumentation using the method of the present invention, showing bilateral fixation with linking members across the spinal midline, as viewed beneath the skin but with the muscle tissue removed to expose details of the underlying vertebrae.

With the foregoing description of the inventive method in mind, attention is directed to the figures. In FIG. 1, a cross-sectional view of a vertebral region of a patient shows a vertebra 10 having pedicle portions 11. In this superior section view, a disc is shown with its annulus 15 intact but with an empty nuclear space 16 after the disc tissue has been resected. Fixation hardware is shown at only one side of the midline ML defined by the spinous process of the vertebra 10. However, as depicted in FIG. 3, fixation instrumentation is implanted on either side of the midline ML. FIG. 3 further shows fixation between adjacent vertebrae, identified as vertebra 10 and 10', with corresponding body portions 10a, transverse processes 10b and 10c, spinous processes 10d, and laminae 10e.

The entry sites 25a and 25b shown in FIG. 1 are used in the disc resection steps of the method. FIGS. 1 and 3 show the location of the portals 26a and 26b through which the disc annulus is removed and the bone graft material introduced. As described above, the entry sites 25a and 25b are nominally 10.0 cm bilaterally from the midline ML. The portals 26a and 26b are oriented so that the disc resection tools can be inserted below the transverse processes 10c of the vertebra at the level of the nerve root.

Referring again to FIG. 1, the skin 20 of the patient is shown dissected from the fascia 22 protecting muscle tissue 23 to provide a suprafascial subcutaneous space 25. An incision 27 is shown through which the fixation hardware is inserted in accordance with the method described above. The fixation hardware includes a bone screw 30, which is preferably a pedicle screw. A fixation plate 40 is mounted on the screw 30, held in place by a nut 42. In the posterior view of FIG. 3, the fixation hardware is also shown as including linking members 44 spanning across the midline between corresponding bone screws 30.

As can be seen most clearly in FIG. 1, the method of the present invention provides a technique for instrumenting adjacent vertebra to facilitate fusion. Implantation of the fixation instrumentation according to the inventive method causes minimal invasion to the patient, with the insertion occurring through a single incision, like incision 27, aligned with each pedicle. Most significantly, the hardware resides within the suprafascial subcutaneous space 25 so that destruction of muscle tissue is not required. With this method, patient morbidity rates are reduces, while healing rates are improved. Since the fixation hardware resides above the muscle layer, removal can be conducted in an out-patient procedure under a local anesthetic.

Referring now to FIG. 2, the details of a bone screw particularly adapted for the present method is shown. The screw 30 includes a distal threaded shank 31, which in the preferred embodiment is configured as a self-tapping pedicle screw in accordance with known technology. The proximal end of the screw 30 includes a machine threaded stem 34, which is threaded for engagement with the nut 42 used to fix the fixation plate 40 and linking member 44. The stem 34 terminates in a driving hex recess 35 which is engaged by an appropriate screw driving tool as known in the art. (Alternatively, a hex projection can be used in lieu of the recess 35, with an appropriate change in the screw driving tool.)

Intermediate the distal shank 31 and proximal stem 34 is a smooth shank portion 32. The smooth shank portion 32 defines a hub 33 near the proximal threaded stem 34. The hub 33 includes a surface 33a configured to support the fixation plate 40. When the nut 42 is tightened onto the proximal stem 34, the fixation plate 40 is locked between the nut and the hub surface 33a. The hub 33 supports the fixation plate to keep it within the suprafascial space 25. The surface 33a is preferably slightly curved to fit within a scalloped fixation plate of known design in the art. The screw 30 is cannulated along its entire length, as represented by the bore 36 provided for guidewire insertion.

The smooth shank portion 32 provides a non-irritating surface for contacting the fascia and muscle tissue. The length of the smooth shank portion 32 is determined by the muscle thickness around the instrumented vertebra, and is generally equal in length to the length of the bone engaging threaded shank 31. In one specific embodiment, the screw 30 has a length measured from the tip of the bone engaging shank 31 to the underside of the mounting hub 33 of 65–75 mm. The bone engaging distal shank 31 has a nominal length of 35 mm which provides optimum engagement with the vertebra. The smooth shank portion 32 accounts for the remainder of the 65–75 mm length, or between 30–40 mm. The machine threaded stem 34 has a length, as measured from surface 33a of the mounting hub 33, that is sufficient to accommodate the fixation plate 40, a nut 42 and a liking member 44. In the specific embodiment, the length of the machine threaded stem 34 is 10–15 mm so that very little of the stem projects beyond the nut. The bone screw 30 can have a diameter of between 5.5–8.5 mm as required for the patient and fixation procedure. It is understood, of course, that the specific dimensions are illustrative of a nominal bone screw configuration. These dimensions can be varied as required for a particular patient or procedure, while still adhering to the basic concepts of the present invention.

Referring now to FIGS. 4A–C, the components of a three component dilator system 50 are shown. As described above, the dilator system is used to facilate implantation of the bone screw 30 into the vertebrae of the patient. The system 50 includes three successively smaller and longer dilator tubes 51, 56 and 61. Each dilator tube is tapered at its respective tip 53, 58 and 63 for atraumatic introduction of the tubes through the skin and tissue of the patient. Each of the tubes is cannulated or hollow as represented by respective bores 52, 57 and 62 there through. The bore 52 in the thinnest dilator tube 51 has a diameter sufficient to accept a guidewire therethrough. The bore 57 in the intermediate diameter dilator tube 56 has a diameter slightly larger than the outer diameter of the dilator tube 51. Likewise, the bore 62 in the largest diameter dilator tube 61 is slightly larger than the outer diameter of the dilator tube 56.

The ends of the smallest and intermediate diameter tubes 51 and 56, ends 54 and 59 respectively, are knurled to provide a gripping surface for removal of the tubes. The lengths of the tubes are graduated so that the smallest diameter tube 51 has the greatest length, while the intermediate tube 56 has a length that is longer than the outermost larger diameter dilator tube 61. This length differential also facilitates sequential removal of the tubes 51 and 56, just prior to and just after the vertebra has been drilled in the instrumentation step or the method.

In one specific embodiment of the three component dilator system 50 of the present invention, the smallest diameter dilator tube 51 has an outer diameter of about 5 mm, a length of 152.5 mm, and a cannulated bore diameter of about 2 mm. The intermediate dilator tube 56 has an outer diameter of 9.4 mm, a length of about 140.0 mm, and a cannulated bore diameter of 5.15 mm (leaving 0.15 mm clearance for insertion of the tube 51). The final dilator tube 61, through which the bone screw 30 is inserted, has an outer diameter of 11.1 mm, a length of 127.0 mm and a cannulated bore diameter of 9.58 mm to receive the intermediate dilator tube 56, as well as the bone screw 30, therethrough.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for implanting a spinal fixation system into a patient having an elongated fixation element configured to be implanted within a patient adjacent the spinal column, comprising the steps of:

providing a cannulated bone engaging fastener having an elongated shank with threads configured for engaging a vertebra at one of the shank, the shank further including means for supporting the elongated fixation element above the muscle tissue and beneath the skin layer of the patient;

inserting a guide pin through the skin layer and muscle tissue of the patient and into a vertebra to be spanned by the elongated fixation element;

successively advancing a plurality of tubular dilators along the guide pin and through the skin layer and muscle tissue, each having a tapered end and each having a successively larger diameter to be received one within the other, the largest diameter dilator being sized to receive the bone engaging fastener therethrough;

removing at least the innermost tubular dilator having the smallest diameter;

advancing a cannulated drill bit along the guide pin and through the innermost remaining dilator to drill a hole to a predetermined depth in the vertebra;

removing the remaining tubular dialators having a diameter less than the diameter of the bone engaging fastener;

advancing a cannulated bone engaging fastener along the guide pin through the innermost remaining dilator and threading the fastener into the drilled hole in the vertebra;

repeating the above steps for a second bone engaging fastener in another vertebra to be spanned by the elongated fixation element; and clamping the elongated fixation element between each of the bone engaging fasteners.

2. The method for implanting a spinal fixation system of claim 1, wherein:

the step of successively advancing a plurality of tubular tissue dilators includes advancing only three dilators, the two smaller dilators having an end opposite said tapered end and a knurled outer surface adjacent said opposite end.

3. The method for implanting a spinal fixation system of claim 1, wherein the plurality of dilators includes only three tubular dilators, the smallest diameter dilator having a diameter smaller than the diameter of the cannulated drill bit, the intermediate diameter dilator having a diameter larger than the diameter of the drill bit.

4. The method for implanting a spinal fixation system of claim 1, wherein:

the step of drilling a hole into the vertebra includes drilling only into the initial one-third of the length of the pedicle of the vertebra;

the step of threading the fastener into the drilled hole includes the steps of;
   initially threading the thatcher into about half of the length of the pedicle;
   verifying the position of the fastener in the pedicle;
   removing the guide wire; and
   threading the fastener to the desired depth in the pedicle.

* * * * *